US008649479B2

(12) United States Patent
De Man et al.

(10) Patent No.: US 8,649,479 B2
(45) Date of Patent: Feb. 11, 2014

(54) SYSTEM AND METHOD FOR BREAST IMAGING USING X-RAY COMPUTED TOMOGRAPHY

(75) Inventors: Bruno Kristiann Bernard De Man, Clifton Park, NY (US); Serge Louis Wilfrid Muller, Guyancourt (FR)

(73) Assignee: General Electric Company, Niskayuna, NY (US)

( * ) Notice: Subject to any disclaimer, the term of this patent is extended or adjusted under 35 U.S.C. 154(b) by 552 days.

(21) Appl. No.: 12/951,690

(22) Filed: Nov. 22, 2010

(65) Prior Publication Data

US 2012/0128120 A1    May 24, 2012

(51) Int. Cl.
A61B 6/03    (2006.01)

(52) U.S. Cl.
USPC .............................. 378/16; 378/37

(58) Field of Classification Search
USPC ............... 378/4, 5, 9, 16, 19, 150, 901, 37
See application file for complete search history.

(56) References Cited

U.S. PATENT DOCUMENTS

| 4,150,293 | A  | * | 4/1979  | Franke ........................ 378/9 |
| 5,999,836 | A  |   | 12/1999 | Nelson et al. |
| 6,480,565 | B1 |   | 11/2002 | Ning |
| 6,501,828 | B1 | * | 12/2002 | Popescu ..................... 378/150 |
| 6,987,831 | B2 | * | 1/2006  | Ning ........................... 378/37 |
| 7,697,657 | B2 | * | 4/2010  | Walter et al. ................. 378/4 |
| 7,711,409 | B2 |   | 5/2010  | Keppel et al. |
| 7,751,528 | B2 |   | 7/2010  | Zhou et al. |
| 2006/0262898 | A1 |  | 11/2006 | Partain et al. |
| 2008/0187095 | A1 |  | 8/2008  | Boone et al. |
| 2009/0171244 | A1 |  | 7/2009  | Ning et al. |
| 2010/0091937 | A1 | * | 4/2010 | Raupach et al. ............. 378/16 |
| 2010/0119033 | A1 | * | 5/2010 | Li et al. ........................ 378/5 |
| 2010/0183213 | A1 |  | 7/2010  | Keppel et al. |
| 2011/0052022 | A1 | * | 3/2011 | Xu et al. .................... 382/131 |

OTHER PUBLICATIONS

Seo et al., "Low-Dose Multidetector Dynamic CT in the Breast: Preliminary Study", Clinical Imaging, vol. 29, Issue 3, pp. 172-178, May 2005.

Bhagtani et al., "Simulated Scatter Performance of an Inverse-Geometry Dedicated Breast CT System", Medical Physics, vol. 36, Issue 3, pp. 788-796, Mar. 2009.

Wang et al., "A Novel Design of Dynamic Phi-Collimator of CT System to Trace Target Scanning Area and Reduce Patient Dose", International Journal of Computer Assisted Radiology and Surgery, (CARS 2009 Computer Assisted Radiology and Surgery, 23rd International Congress and Exhibition), vol. 4, Supplement 1, pp. 5-8, Jun. 23-27, 2009.

(Continued)

Primary Examiner — Irakli Kiknadze
(74) Attorney, Agent, or Firm — Jenifer Haeckl

(57) ABSTRACT

A system and method for breast imaging using x-ray computed tomography (CT) are provided. One system includes a rotating gantry, an x-ray source coupled to the gantry for generating an x-ray beam and an x-ray detector coupled to the gantry for detecting x-rays of the x-ray beam. The system further includes an adjustable collimator coupled to the x-ray source and configured to adjust a focus of the x-ray beam generated by the x-ray source. The x system also includes a controller configured to control the collimator to adjust the focus on a region of interest (ROI) and to control a beam intensity for the x-ray beam generated by the x-ray source during a scan.

34 Claims, 7 Drawing Sheets

(56) References Cited

OTHER PUBLICATIONS

Lai et al., "Reduction in X-ray Scatter and Radiation Dose for Volume-of-Interest (VOI) Cone Beam Breast CT—A Phantom Study", Physics in Medicine and Biology, vol. 54, No. 21, pp. 6691-6709, Nov. 7, 2009.

Huy et al., "Radiation Dose Reduction using a CdZnTe-based Computed Tomography System: Comparison to Flat-Panel Detectors", Medical Physics, vol. 37, Issue 3, pp. 1225-1236, Mar. 2010.

* cited by examiner

SYSTEM AND METHOD FOR BREAST IMAGING USING X-RAY COMPUTED TOMOGRAPHY

BACKGROUND OF THE INVENTION

The subject matter disclosed herein relates generally to imaging systems, and more particularly to systems and methods for x-ray breast imaging.

Mammography is an x-ray imaging modality used to scan breasts for screening, diagnosis and management. The effectiveness of mammography is affected by numerous factors, including radiation scatter, noise and overlapping anatomical structures due to conventional techniques of x-ray projection imaging.

Dedicated systems are known for breast imaging. For example, a digital breast tomosynthesis (DBT) or mammography-tomography (mammo-tomo) system is a dedicated mammography system that acquires several (e.g., tens of) angularly offset projection images and reconstructs three-dimensional (3D) image datasets, which can have reduced anatomical overlap. However, although these conventional DBT systems may partially overcome the limitations of standard mammography systems, DBT systems still have limited depth resolution. Additionally, associated artifacts and scatter are still issues when using the DBT systems.

BRIEF DESCRIPTION OF THE INVENTION

In accordance with an embodiment, an x-ray computed tomography (CT) system is provided that includes a rotating gantry, an x-ray source coupled to the gantry for generating an x-ray beam and an x-ray detector coupled to the gantry for detecting x-rays of the x-ray beam. The x-ray CT system further includes an adjustable collimator coupled to the x-ray source and configured to adjust a focus of the x-ray beam generated by the x-ray source. The x-ray CT system also includes a controller configured to control the collimator to adjust the focus on a region of interest (ROI) and to control a beam intensity for the x-ray beam generated by the x-ray source during a scan.

In accordance with another embodiment, an x-ray computed tomography (CT) system is provided that includes a rotating gantry, a plurality of x-ray sources coupled to the gantry for generating x-ray beams and an x-ray detector coupled to the gantry for detecting x-rays of the x-ray beams. The x-ray CT system further includes a controller configured to independently control the plurality of x-ray sources to selectively generate x-ray beams to adjust the focus on a region of interest (ROI) and to control a beam intensity for the x-ray beams generated by the plurality of x-ray sources during a scan.

In accordance with yet another embodiment, a method to control the operation of a rotating computed tomography (CT) imaging system to perform organ specific imaging is provided. The method includes identifying a patient orientation within a bore of the CT imaging system and determining a gantry angle of the CT imaging system, with the gantry supporting at least one x-ray source and an x-ray detector. The method further includes adjusting, during a scan with the CT imaging system, a focus of the x-ray source and a beam intensity generated by the at least one x-ray source based on an angular orientation of the gantry.

DETAILED DESCRIPTION OF THE INVENTION

Figure 1:
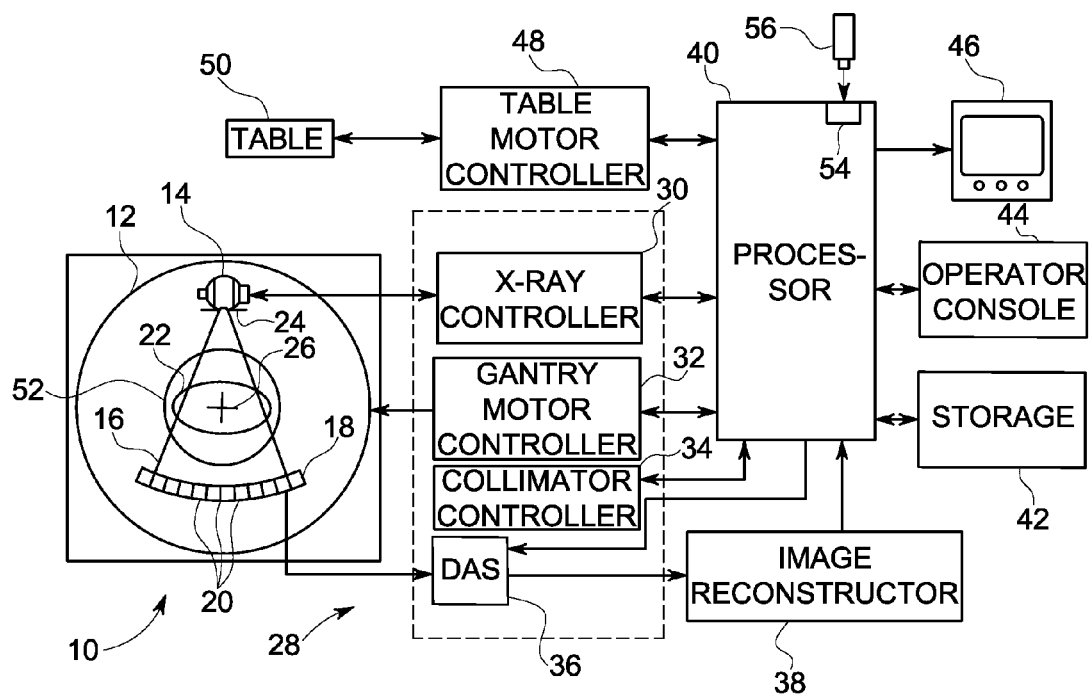
FIG. 1 is a block diagram illustrating an x-ray computed tomography (CT) imaging system formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also, as used herein, the phrase "reconstructing an image" is not intended to exclude embodiments in which data representing an image is generated, but a viewable image is not. However, many embodiments generate (or are configured to generate) at least one viewable image.

Various embodiments provide a system and method for x-ray computed tomography (CT) breast imaging. The CT breast imaging is performed using dynamic region of interest (ROI) collimation control with varying x-ray beam intensity.

At least one technical effect of the various embodiments is the ability to perform breast imaging using an imaging system that is not configured for dedicated breast imaging. For example, by practicing at least some embodiments, breast imaging may be performed using a CT architecture with a patient imaged in a supine position.

FIG. 1 illustrates a simplified block diagram of an x-ray CT system 10 operable to perform breast imaging in accordance with various embodiments. The x-ray CT system 10 may be configured as a multi-slice scanning imaging system that includes a gantry 12, which may be representative of a third generation CT imaging system as described in more detail herein. The gantry 12 generally includes (e.g., supports thereon) an x-ray source 14 (also referred to as an x-ray tube) that projects an x-ray beam 16 towards a detector array 18 on the opposite side of the gantry 12. The detector array 18 is formed by a plurality of detector rows (not shown) including a plurality of detector elements 20 that together sense the projected x-rays that pass through an object, such as a patient 22 (e.g., a female patient having breast scanning performed) positioned in a supine (or optionally prone or standing) position between the detector array 18 and the x-ray source 14.

A collimator 24 is provided in combination with the x-ray source 14 to collimate and focus the x-ray beam 16. In various embodiments, the intensity level and the collimation of the generated x-ray beam 16 are dynamically controlled and adjusted. For example, as described in more detail herein, dynamic breast ROI collimation and sensitive organ power modulation are provided in accordance with various embodiments.

With respect to the detector array 18, each detector element 20 produces an electrical signal that represents the intensity of an impinging x-ray beam and hence can be used to estimate the attenuation of the beam as the beam passes through the patient 22. During a scan to acquire x-ray projection data, the gantry 12 and the components mounted therein rotate about a center of rotation 26. It should be noted that although only a single row of detector elements 20 (i.e., a detector row) is shown, the detector array 18 in various embodiments is a multi-slice detector array having a plurality of parallel detector rows of detector elements 20, such that projection data corresponding to a plurality of quasi-parallel or parallel slices can be acquired simultaneously during a scan.

Rotation of the components on the gantry 12 and operation of the x-ray source 14 and collimator 24 are governed by a control mechanism 28 of the CT system 10. The control mechanism 28 includes an x-ray controller 30 that provides power and timing signals to the x-ray source 14, a gantry motor controller 32 that controls the rotational speed and position of components on the gantry 12, and a collimator controller 34 that controls collimation of the x-ray source 14 to adjust and define an ROI. For example, a field of view (FOV) of the collimator 24 is adjusted using dynamic collimation.

A data acquisition system (DAS) 36 in the control mechanism 28 samples analog data from the detector elements 20 and converts the data to digital signals for subsequent processing. An image reconstructor 38 receives sampled and digitized x-ray data from the DAS 36 and performs image reconstruction. The reconstructed image is communicated to a processor 40 (e.g., a computer), which stores the image in a storage device 42. The image reconstructor 38 can be specialized hardware or computer programs executing on the processor 40, for example, as a module.

The processor 40 also receives commands and scanning parameters from an operator via an operator console 44 that includes input devices, such as a keyboard, mouse, etc. An associated display 46 is provided, which may be any suitable display type that allows the operator to view the reconstructed image(s) and other data from the processor 40. The operator supplied commands and parameters may be used by the processor 40 to provide control signals and information to the DAS 36, x-ray controller 30, gantry motor controller 32 and collimator controller 34 as described in more detail herein. In addition, the processor 40 operates a table motor controller 48, which controls a motorized patient table 50 to position the patient 22 in the gantry 12. Particularly, the table 50 moves portions of the patient 22 through a gantry opening 52. It should be noted that the patient 22 (or a portion of the patient 22) may be moved into the gantry 12 and during imaging remain stationary during rotation of the gantry 12 or may move the patient 22 through the opening 52 during as the gantry 12 rotates.

In various embodiments, the processor 40 includes a device 54, for example, a CD-ROM drive, a DVD drive, a magnetic optical disk (MOD) device, a USB port, or any other digital device including a network connecting device such as an Ethernet device for reading instructions and/or data from a computer-readable medium 56, such as a floppy disk, a CD-ROM, a DVD, a flash memory drive (illustrated in FIG. 1) or another digital source such as a network or the Internet, as well as yet to be developed digital means. In other embodiments, the processor 40 executes instructions stored in firmware (not shown). The processor 40 is programmed to perform functions described herein, and as used herein, the term processor is not limited to just those integrated circuits referred to in the art as computers, but broadly refers to computers, microcontrollers, microcomputers, programmable logic controllers, application specific integrated circuits, and other programmable circuits, and these terms are used interchangeably herein.

Although the above-described embodiment refers to a third generation CT system, the methods described herein equally apply to fourth generation CT systems (stationary detector-rotating x-ray source) and fifth generation CT systems (stationary detector and x-ray source). Additionally, it is contemplated that the benefits of the various embodiments accrue to imaging modalities other than CT. Further, although the herein described methods and apparatus are described in a particular medical setting, it is also contemplated that the benefits of the various embodiments accrue to other applications or settings.

Figure 2:
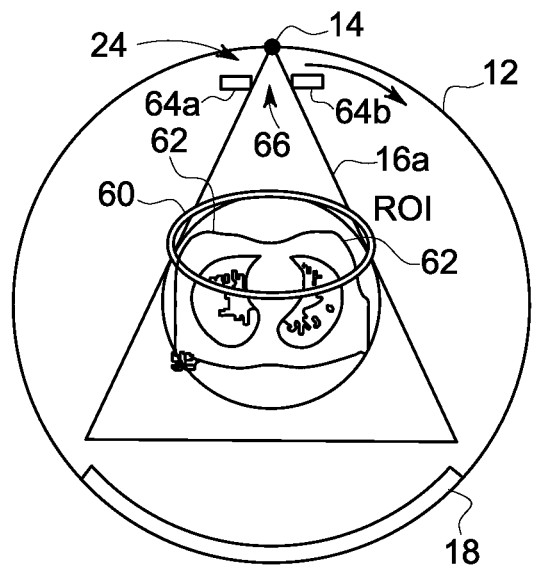
FIG. 2 is a diagram illustrating x-ray CT breast imaging at one gantry position in accordance with various embodiments.
Figure 3:
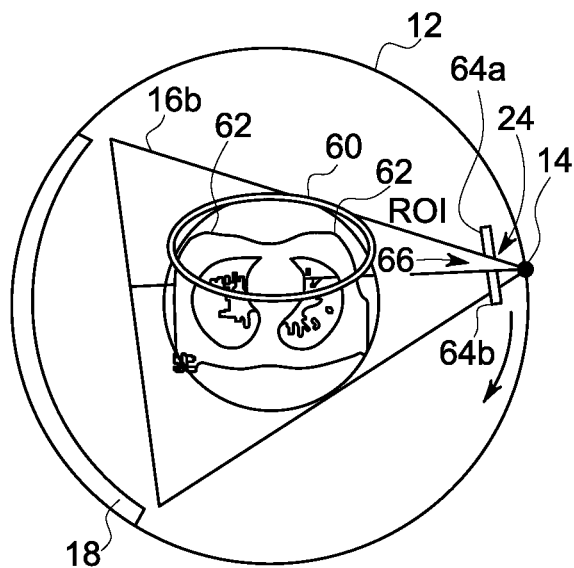
FIG. 3 is a diagram illustrating x-ray CT breast imaging at another gantry position in accordance with various embodiments.
Figure 4:
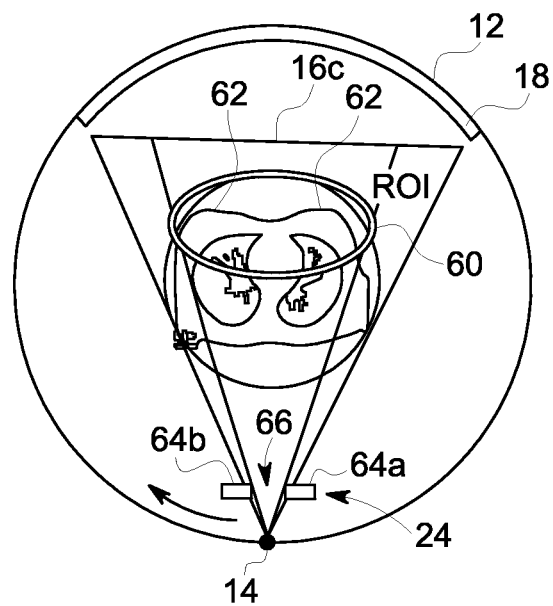
FIG. 4 is a diagram illustrating x-ray CT breast imaging at another gantry position in accordance with various embodiments.

In operation, various embodiments control the x-ray source power and collimation of the x-ray beams generated by the x-ray source as illustrated in FIGS. 2 through 4, such as based on different gantry positions or angles. For example, as illustrated, the x-ray source 14 projects the x-ray beam 16, which may be an x-ray fan-beam, that is collimated to lie within an ROI 60 of an X-Y plane of a Cartesian coordinate system and generally referred to as an "imaging plane". The power of the x-ray source 14 is also controlled at different gantry positions, such as based on the angle at which the x-ray beam 16 intersects the patient 22 relative to the ROI 60, which in this embodiment are breasts 62 of the patient 22. It should be noted that although the x-ray beam 16 is illustrated as a fan-beam, other variations and x-ray beam geometries are contemplated. For example, in some embodiments, the x-ray beam 16 is a parallel beam.

The x-ray beam 16 passes through the patient 22 (shown in FIG. 1) after being attenuated by the patient 22, and impinges on the detector array 18. The intensity of the attenuated radiation beam received at the detector array 18 is dependent upon the attenuation of the x-ray beam 16 by the patient 22. Each detector element 20 of the detector array 18 produces a separate electrical signal that is a measurement of the beam intensity at the detector location. The intensity measurements from all the detectors are acquired separately to produce a transmission profile and based on x-ray beams 16 having different intensities.

In third generation CT systems, the x-ray source 14 and the detector array 18 are rotated with the gantry 12 within the imaging plane and around the patient 22 such that the angle at which the x-ray beam 16 intersects the patient 22 constantly changes. A group of x-ray attenuation measurements, i.e., projection data, from the detector array 18 at one gantry angle is referred to as a "view". A "scan" of the object comprises a set of views made at different gantry angles, or view angles, during one half or more revolutions of the x-ray source and detector. Thus, during one half or more revolutions, the power of the x-ray source 14 and the collimation by the collimator 24 (e.g., the size of the collimator opening) is dynamically varied.

Various embodiments may be performed using a CT scan wherein the x-ray source 14 and the detector array 18 rotate around the patient 22. The patient table 50 (shown in FIG. 1) supporting the patient 22 may remain stationary during the scan (axial scan) or move during the scan (helical scan). In an axial scan, projection data is acquired at each of a plurality of stationary positions to construct an image or volume that corresponds to cross-sectional information of the patient 22. Thus, the patient 22 remains stationary during scanning at each axial location of the patient 22. Any suitable method for image reconstruction may be used, such as a filtered back-projection technique. This process converts the attenuation measurements from a scan into integers called "CT numbers" or "Hounsfield units" (HU), which are used to control the brightness of a corresponding pixel of a displayed image.

A "helical" scan (or spiral scan) may be performed, for example, to reduce the total scan time. To perform a "helical" scan, the patient 22 is moved while the data for the prescribed number of slices is acquired. During helical scan operation, a single helix is generated by combining gantry rotation and patient translation. The helical scan results in projection data from which images in each prescribed slice or volume may be reconstructed. Reconstruction algorithms for helical scanning may use helical weighing algorithms that weights the collected data as a function of the view angle and detector channel index. Specifically, prior to or during a back projection process, the data is weighted according to a helical weighing factor, which is a function of both the gantry angle and detector angle. The weighted data is then processed to generate CT numbers and to construct an image that corresponds to cross-sectional information taken through the patient 22.

Multi-slice CT may be used wherein multiple rows of projection data are acquired simultaneously at any point in time, which also reduces the total scan time. When combined with a helical scan mode, the system generates a single helix of cone beam projection data. Similar to the single slice helical weighting scheme, a method can be derived to multiply the weight with the projection data prior to or during the backprojection process.

It should be noted that in various embodiments, a peripheral ROI, such as the breast region, may be reconstructed even when only projection lines through the ROI are measured and projection lines outside the ROI are not collected, for example, a derivative backprojection technique or by iterative reconstruction or by statistical reconstruction.

During rotation of the x-ray source 14 and the detector array 18 around the patient 22, in particular, during a third-generation CT scan, the x-ray beam 16 is dynamically collimated and the power level of the x-ray source 14 adjusted for breast CT imaging. For example, the dynamic collimation and power level adjustment may be configured or optimized for breast CT imaging. As illustrated in FIGS. 2 through 4, an x-ray beam 16 is dynamically collimated such that x-rays are blocked in regions or areas outside of the ROI 60, which changes with different gantry angles. For example, real-time control of activators or driving means (e.g., motors) driving the position of two or more metal collimation plates 64 (two plates 64 are illustrated) may be provided by the collimator controller 34 (shown in FIG. 1). This control may include moving one or both of the collimation plates 64 to open or close a collimator hole 66 such that the x-ray beam 16 is focused on the ROI 60 throughout the rotation of the gantry 12. Thus, each collimation plate 64 may move independently and different amounts to vary the direction and focus of the x-ray beam 16. It should be noted that real-time refers to controlling operation, for example, during an imaging scan, which may be while the gantry 12 is stationary or moving, or while the patient table 50 is stationary or moving.

In addition to collimation control, the various embodiments also dynamically and in real-time control the beam intensity by varying the power of the x-ray source 14 (e.g., x-ray tube current or voltage) to change the intensity of the x-ray beam 16. For example, the beam intensity can be modulated such that more or less x-rays forming the x-ray beam 16 are generated and transmitted. Thus, tube current modulation (referred to as mA modulation) and/or tube voltage modulation (referred to as kV modulation) may be provided as desired as needed.

Referring to the three gantry positions illustrated in FIGS. 2 through 4, the collimation and beam intensity are varied and may be different in each of these positions. However, it should be noted that the collimation and beam intensity at one or more of the gantry positions (as the gantry 12 rotates one revolution) may be the same. In FIG. 2, the gantry 12 is positioned with the x-ray source 14 above the patient 22 and the detector array 18 below the patient 22, with the patient 22 in a supine position, for example, supported on his or her back on the patient table 50 (shown in FIG. 1). In this gantry position, the collimator 24 is in an open state such that the x-ray beam 16a irradiates the entire front of the patient 22 to encompass the ROI 60. This collimator 24 configuration is generally referred to as full fan-beam operation. The intensity of the x-ray beam 16 is reduced in this gantry position, for example, having a reduced mA or kV relative to the gantry positions illustrated in FIGS. 3 and 4.

In FIG. 3, the gantry 12 is positioned with the x-ray source 14 on one side of the patient 22 and the detector array 18 positioned on the other side of the patient 22. In this gantry position, the collimator 24 is adjusted such that one or both of the collimation plates 64 are moved to focus the x-ray beam 16b such that the fan-beam only irradiates the ROI 60. For example, the collimation plate 64b may be moved to block x-rays from irradiating the lower portion of the patient 22 while the collimation plate 64a is not moved to allow x-ray to irradiate an upper portion of the patient 22. This collimator 24 configuration is generally referred to as partial-fan-beam operation, which in this embodiment is less than half of the full fan-beam operation. However, it should be noted that fan-beam width may be varied to different degrees based on the gantry position, the size of the patient, etc. Thus, the fan-beam may be narrowed or widened, as well as directed or focused as desired or needed. The intensity of the x-ray beam 16 is increased in this gantry position relative to the gantry position shown in FIG. 2, for example, having an increased mA or kV relative to the gantry position illustrated in FIG. 2, but less intensity than the gantry position illustrated in FIG. 4.

In FIG. 4, the gantry 12 is positioned with the x-ray source 14 below the patient 22 and the detector array 18 above the patient 22. In this gantry position, the collimator 24 is adjusted such that one or both of the collimation plates 64 are moved to focus the x-ray beam 16c such that the fan-beam irradiates the ROI 60, which is now on the opposite side of the patient 22 from the x-ray source 14. In this gantry position, both of the collimation plates 64a and 64b may be moved to block x-rays from irradiating portions of the side of the patient 22 outside of the ROI 60 such that the fan-beam is narrowed with the width reduced on each side of the fan-beam. This collimator 24 configuration is generally referred to as reduced fan-beam operation, which in this embodiment is more than half of the full fan-beam operation, but with blocked sides of the fan-beam. However, it should be noted that fan-beam width may be varied to different degrees based on the gantry position, the size of the patient, etc. Thus, the fan-beam again may be narrowed or widened, as well as directed or focused as desired or needed. The intensity of the x-ray beam 16 is increased in this gantry position relative to the gantry positions shown in FIGS. 2 and 3, for example, having an increased mA or kV relative to the gantry positions illustrated in FIGS. 2 and 3. Thus, the lowest beam intensity is provided in the orientation in FIG. 2 with increasing beam intensities in the orientations of FIGS. 3 and 4, respectively.

Thus, in various embodiments, beam collimation is controlled to focus the x-ray beam 16 on the ROI 60, while varying beam intensity based on whether the beam will be attenuated before the beam reaches the sensitive organ region (e.g., ROI 60) as opposed to when the beam first hits the sensitive organ region and the passes through the rest of the body (of the patient 22). Accordingly, optimized breast CT scanning may be performed with dynamic breast ROI collimation (to focus on the breasts 62) and sensitive organ modulation (to reduce beam intensity when organs, such as the breasts 62 are closer to the x-ray source 14). As illustrated in FIGS. 2 through 4, in addition to ROI collimation to focus the beam on the breasts 62, beam intensity is modulated such that more x-rays are transmitted through the back of the patient 22 and fewer (or no) x-rays are transmitted directly to the sensitive breast region. Accordingly, beam intensity modulation of x-rays that are limited to passing through the ROI 60 is provided in some embodiments, with the x-ray beam intensity is highest from the back of the patient 22 and lowest from the front of the patient 22.

It should be noted that the dynamic ROI collimation and sensitive organ power modulation are not limited to x-ray CT imaging of the breasts 62. The various embodiments may be used to image different regions of the patient 22, such as different organs. It also should be noted that modifications and variations are contemplated. For example, although the dynamic collimation scheme described herein cuts off or blocks completely the radiation behind the collimation plates 64, a dynamic bowtie type filter may be used where the x-ray profile is gradually or incompletely cut off or blocked.

For example, another embodiment includes applying the systems and methods described herein to x-ray CT imaging of the lungs. In this application, patient radiation dose may be reduced or minimized, while enabling good or improved image quality, for example for lung screening applications. Additionally, in this application, the ROI may correspond to the lung region and the sensitive organ region may correspond to the breast region. The ROI collimation and the multiple source firing sequence is adjusted in order to include the lung region and avoid the breast region. The beam intensity modulation is also selected to reduce or minimize radiation dose to the breast region and to increase or maximize image quality in the lung region. In addition, the use of a photon-counting detector can provide high x-ray detection efficiency. In addition, statistical or iterative reconstruction techniques may be used to improve or optimize the image quality for a given low beam intensity profile.

It also should be noted that the control of the beam intensity and beam collimation may be varied as desired or needed. For example, when imaging the breasts 62, the system may be controlled to reduce or stop exposure of the breasts 62 to the x-ray beam 16 when tissue is between the breasts 62 and the x-ray source 14 and to expose or increase exposure of the x-ray beam 16 to the breasts 62 when there is no tissue or a lesser amount of tissue between the breasts 62 and the x-ray source 14.

Figure 5:
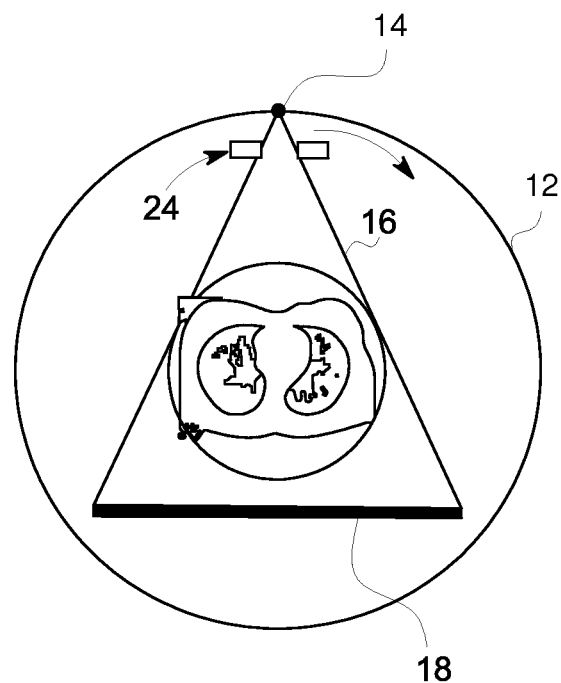
FIG. 5 is a diagram illustrating high resolution imaging in accordance with various embodiments.
Figure 6:
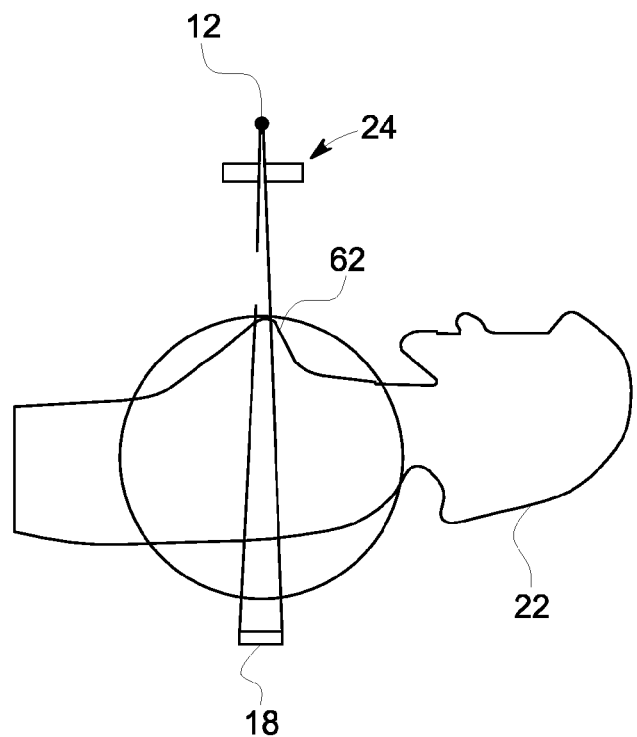
FIG. 6 is a diagram illustrating a patient in a supine position in accordance with various embodiments.

The components of the CT system 10 may be configured based on the imaging to be performed, such as the breast imaging described herein. For example, for high spatial resolution, the focal spot in various embodiments is a very small focal spot, such as between 0.2 mm and 0.6 mm, which is illustrated in FIGS. 5 and 6 (showing transaxial and longitudinal views, respectively). The focal spot can also be deflected in the xy plane, as well as along the z direction to provide over-sampling and improved spatial resolution and reduced aliasing artifacts. In various embodiments, the detector array 18 includes the plurality of detector elements 20 having a small cell size, such as between 0.1 mm and 0.6 mm. In operation with these configurations, and for dose-efficiency, the detector array 18 is configured as a photon-counting detector. However, as described herein, the detector array 18 can be a 1D linear array or include multiple detector rows defining a 2D array. Additionally, in various embodiments, the cone-angle is very narrow and limited to a single or a few detector rows, which limits the relative amount of scattered radiation detected by the detector array 18. Thus, a helical scan protocol to cover the entire breast region in a shorter amount of time may be used.

It should be noted that focal spot size and cell size may be smaller or larger, such as smaller for micro-focus x-ray sources having a spot size smaller than 0.2 mm.

Figure 7:
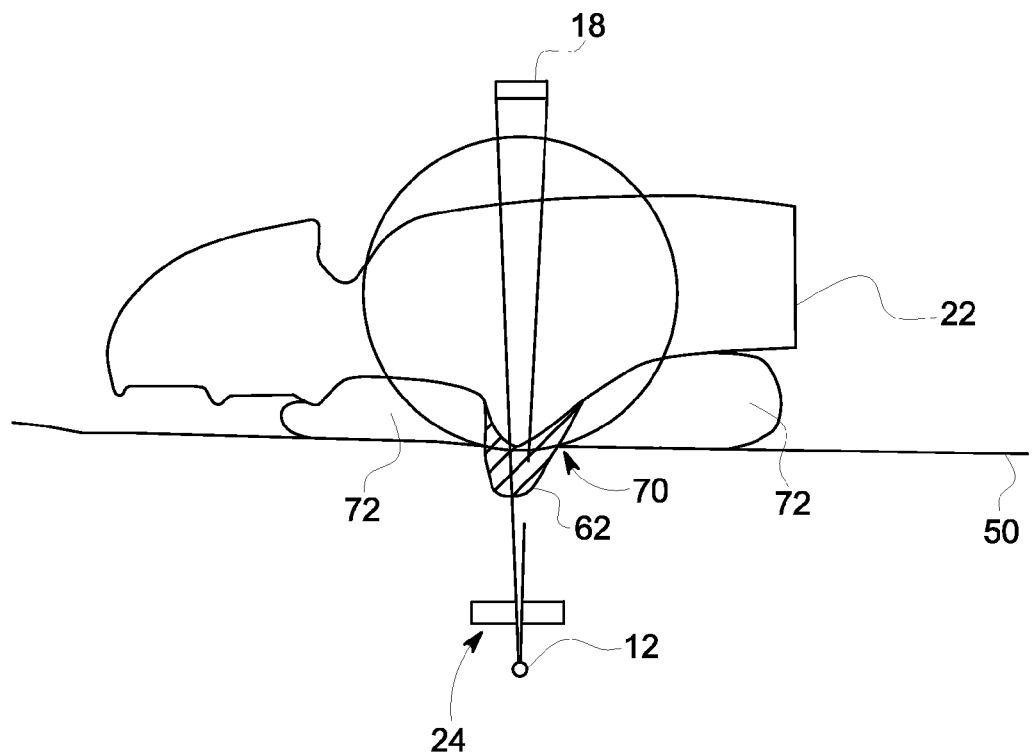
FIG. 7 is a diagram illustrating a patient in a prone position in accordance with various embodiments.

In some embodiments, instead of the patient 22 positioned in a supine position for imaging as illustrated in FIG. 6, the patient 22 may be positioned in a prone position on the patient table 50 as illustrated in FIG. 7. In this embodiment, a space is provided for the breasts 62 to extend away from the patient's chest. In some embodiments, an opening 70 is provided in the patient table 50 to allow the breasts 62 to extend therethrough and away from the patient's chest due to the force of gravity. It should be noted that one or more spacers, illustrated as cushions 72 may be provided underneath the chest above and/or below the breast region of the patient 22. It also should be noted that more of less cushions 72, or different sizes and shapes of cushions 72 may be provided, such as based on the height, weight, etc of the patient 22. In some embodiments, a pulling force optionally may be applied to the breasts 62, for example, such as using any suitable suction device.

It should be noted that other patient positions are contemplated. For example, the patient 22 may be standing or in an elevated position between a supine and a sitting position.

In embodiments where the patient 22 is positioned in prone position, the imaging operation including the rotation and control of the components can be performed in a similar manner to the supine position using a rotating CT system. It should be noted that different types of CT imaging systems or the CT system 10 operating differently may be provided. For example, breast imaging in accordance with various embodiments may be performed using multi-energy CT by alternatingly operating the x-ray source 14 at higher and lower tube voltages. Alternatively, multi-energy CT can be provided by having an energy-sensitive detector, such as a photon-counting detector.

Figure 10:
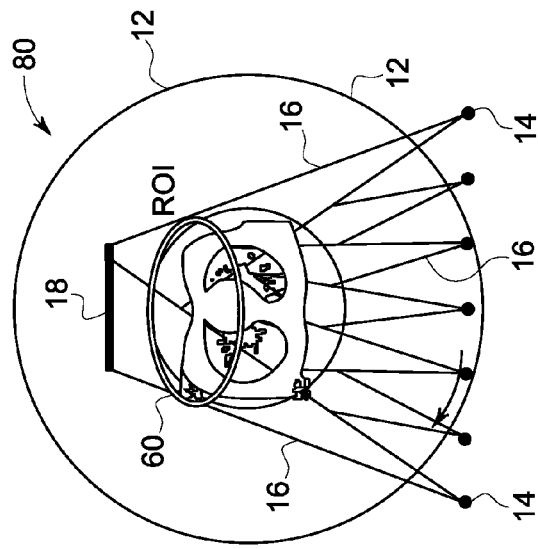
FIG. 10 is a diagram illustrating x-ray CT breast imaging at another gantry position in accordance with other various embodiments.
Figure 9:
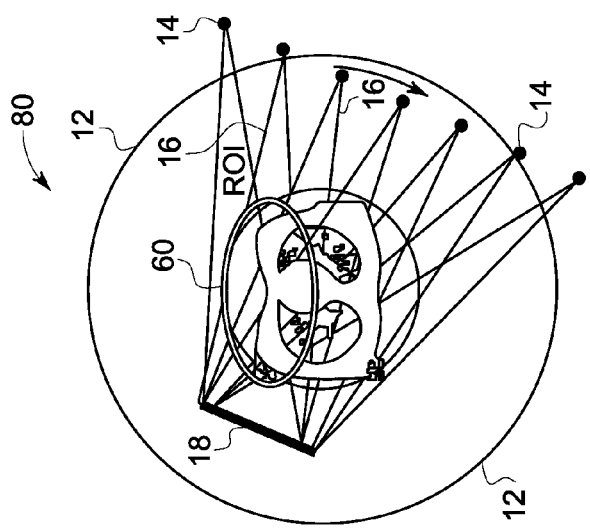
FIG. 9 is a diagram illustrating x-ray CT breast imaging at another gantry position in accordance with other various embodiments.
Figure 8:
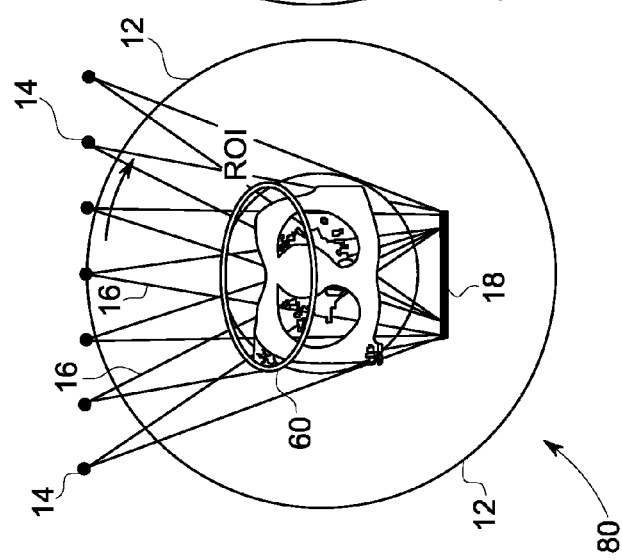
FIG. 8 is a diagram illustrating x-ray CT breast imaging at one gantry position in accordance with other various embodiments.

The various embodiments also may be implemented with a multi-source CT system 80 as illustrated in FIGS. 8 through 10, wherein like reference numerals represent like or similar parts. In this embodiment, dynamic breast ROI focusing and sensitive organ power modulation are provided using a plurality of x-ray sources 14 without dynamic collimators 24. In operation, the x-ray sources 14 may generate x-ray beams 16 sequentially. It should be noted that the number and positioning of the x-ray sources 14 may be changed, such that more or less x-ray sources 14 may be provided, and spaced evenly or unevenly about the patient 22.

In operation, for breast CT scanning, only the x-ray sources 14 having x-ray fan beams that intersect the breast region at the current view angle, namely the ROI 60, are operated or fired, such that the x-ray sources 14 are independently or selectively controlled to transmit x-ray beams 16. It should be noted that "fired" generally refers to an x-ray source 14 generating and transmitting an x-ray beam 16. The other x-ray sources 14 are skipped or operated at a lower frequency. Thus, as illustrated in FIG. 8, with the gantry 12 positioned such that the x-ray source 14 is above the patient 22 and the detector array 18 is positioned below the patient 22, not all of the x-ray sources 14 generate x-ray beams 16. For example, the outer two x-ray sources 14 are not fired such that a narrower x-ray beam coverage area is defined and focused on the ROI 60. When the gantry 12 is positioned as shown in FIG. 9, such that the x-ray source 14 is on one side of the patient 22 and the detector array 18 is on the other side of the patient 22, an even lesser amount of x-ray sources 14 are fired, which is illustrated as two x-ray sources 14. The x-ray sources 14 that are operable and fired are the x-ray sources 14 that generate fan-beams to irradiate the ROI 60. When the gantry is positioned as shown in FIG. 10, such that the x-ray source is below the patient 22 and the detector array 18 is above the patient 22, a greater number of x-ray sources 14 are fired, which in this embodiment includes all of the x-ray sources 14.

Thus, in this embodiment a focused irradiation region is defined by controlling which of the x-ray sources 14 are generating x-ray beams 16 to cover the ROI 60, instead of using a collimator 24 as illustrated in FIGS. 2 through 4. However, it should be noted that ROI collimation also may be provided in the embodiment illustrated in FIGS. 8 through 10. Additionally, the beam intensity is controlled similar to the embodiment illustrated in FIGS. 2 through 4 such that the beam intensity at the gantry orientation of FIG. 10 is higher than the beam intensity for the gantry orientation of FIG. 9, which has a higher beam intensity than the gantry orientation of FIG. 8. Thus, the intensity of x-ray beams 16 may be adjusted for each x-ray pulse for optimal dose-efficiency. Accordingly, in various embodiments, more x-rays are provided from the back of the patient 22 and fewer when the x-ray source 14 is directly in front of the breast region. Thus, the flux from each of the x-ray sources 14 may be modulated and controlled such that more or less x-rays are transmitted to a particular area based on the number of x-ray sources 14 used and the location of the x-ray sources 14.

The various embodiments also may adjust or compensate for different factors or variables, such as respiratory and heart motion. In some embodiments, respiratory motion is reduced or eliminated by having the patient 22 hold his or her breath such that scan can be completed within a single breath hold. With respect to cardiac motion, the various embodiments may be performed in combination with any suitable electrocardiography (ECG)-gating or motion compensation techniques to suppress cardiac motion blur or motion artifacts.

Figure 11:
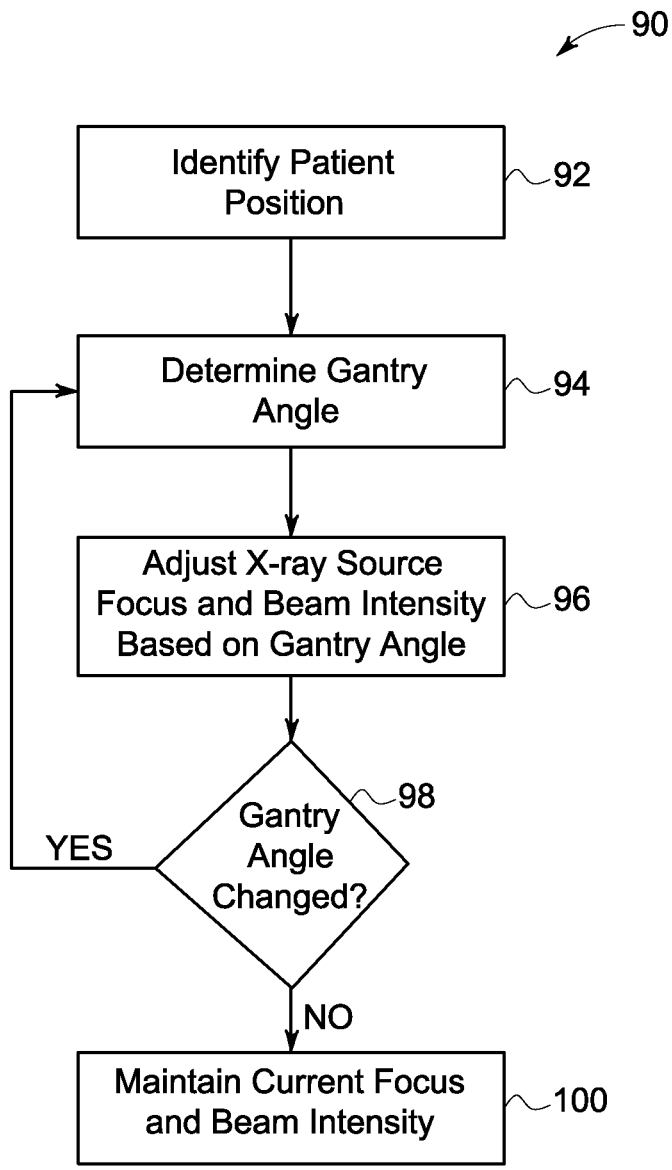
FIG. 11 is a flowchart of a method to control the operation of a rotating CT imaging system to perform organ specific imaging in accordance with various embodiments.

Various embodiments also may provide a method 90 as illustrated in FIG. 11 to control the operation of a rotating CT imaging system to perform organ specific imaging, for example, breast imaging. In particular, the method 90 includes identifying a patient position at 92, for example, whether the patient is supported in a supine or prone position within the gantry of the CT imaging system. This determination may be made based upon a user input identifying the position or may be determined automatically, for example, using a suitable sensor or camera system.

Thereafter, upon initiation of an imaging scan, a determination is made at 94 as to the current gantry angle. For example, encoders on an x-ray source, detector or other portion of the rotating gantry may provide position information identifying the current angular position or orientation of the gantry. Accordingly, based on known mounting locations of the x-ray source and detector on the gantry, and the identified patient position, the position of the x-ray source and detector relative to the patient may be determined. For example, a determination can be made as to whether the x-ray source is in front of the patient, behind the patient or at some position therebetween.

Based on the determined gantry angle, the collimation or focus of the x-ray source and the beam intensity as generated by the x-ray source are adjusted at 96. For example, the focus may be adjusted using dynamic collimation as described herein to cover an ROI and the x-ray beam intensity may be varied (e.g., tube voltage or tube current) based on whether the x-ray source is closer to the front or back of the patient.

Thereafter, a determination is made at 98 as to whether the gantry has moved such that the gantry angle has changed. If the gantry angle has not changed, then at 100 the current focus and beam intensity level are maintained. If the gantry angle has changed, then the new gantry angle is determined again at 94 and the method proceeds as described above.

It should be noted that the focus of the x-ray source and/or the varying of the beam intensity as generated by the x-ray source may be adjusted at each gantry position or may be maintained at different gantry positions. In some embodiments, the focus of the x-ray source and the beam intensity as generated by the x-ray source are incrementally changed at each gantry angle.

Figure 12:
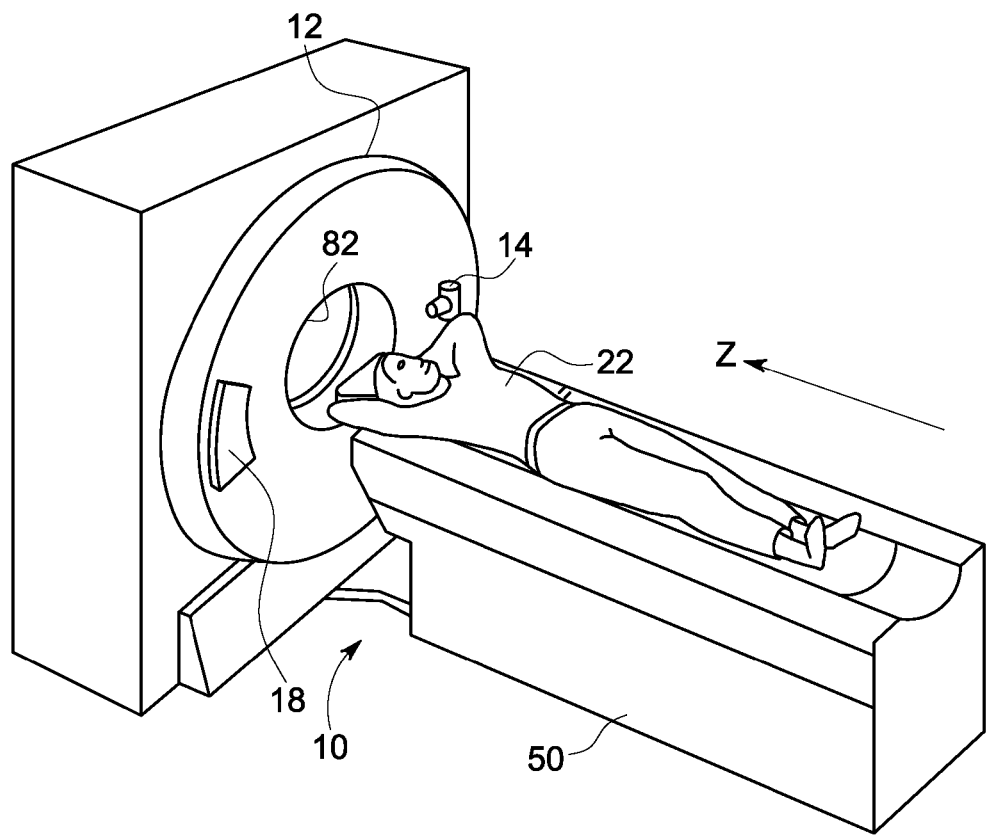
FIG. 12 is a perspective view of an x-ray CT imaging system formed in accordance with various embodiments.

Thus, in various embodiments, breast CT imaging may be provided with a CT imaging system, for example, the CT imaging system 10 that rotates around a patient 22 (or a portion of the patient 22) within a bore 82 defining the gantry opening 52 (shown in FIG. 1) as illustrated in FIG. 12, with the patient 22 in a supine (as shown in FIG. 12) or prone position. Additionally, ROI collimation combined with mA of kV modulation are provided. Further, a photon-counting detector with a small detector cell size may be provided that operates in a configuration wherein a small focal spot is generated.

Other modifications and variations are contemplated. For example, the breasts of the patient may be positioned off-centered on a diameter of the FOV to reduce patient exposure outside of the breast region. As another example, a very-low dose initial acquisition may be performed to manually or automatically select the ROI in order to adapt to patient conformance, such as patient size, etc.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An x-ray computed tomography (CT) system comprising:
a rotating gantry;
an x-ray source coupled to the gantry for generating an x-ray beam;
an x-ray detector coupled to the gantry for detecting x-rays of the x-ray beam;
an adjustable collimator coupled to the x-ray source and configured to adjust a focus of the x-ray beam generated by the x-ray source;
a controller configured to control the collimator to adjust the focus on a region of interest (ROI) and to control a beam intensity for the x-ray beam generated by the x-ray source during a scan; and
a patient table supporting a patient thereon and wherein the controller is configured to decrease the beam intensity when the x-ray source is closer to the ROI of the patient and to increase the beam intensity when the x-ray source is farther away from the ROI.

2. The x-ray CT system of claim 1, wherein the controller is configured to dynamically adjust the adjustable collimator in real-time.

3. The x-ray CT system of claim 1, wherein the adjustable collimator comprises movable collimation plates configured to adjust an opening through which x-rays from the x-ray source are transmitted to change the focus during an image scan.

4. The x-ray CT system of claim 3, wherein the collimation plates are independently adjustable.

5. The x-ray CT system of claim 1, wherein the controller is configured to adjust one of a tube current or a tube voltage of the x-ray source.

6. The x-ray CT system of claim 1, wherein the controller is configured to adjust the focus or beam intensity based on an angular orientation of the rotating gantry.

7. The x-ray CT system of claim 1, wherein the ROI comprises a breast region.

8. The x-ray CT system of claim 1, wherein the ROI comprises a lung region.

9. The x-ray CT system of claim 1, wherein the x-ray detector comprises a photon-counting detector.

10. The x-ray CT system of claim 1, further comprising a patient table and wherein a patient is supported in a supine position within a bore of the gantry.

11. The x-ray CT system of claim 1, further comprising a patient table and wherein a patient is supported in a prone position within a bore of the gantry.

12. The x-ray CT system of claim 1, wherein the x-ray detector comprises a plurality of elements having a cell size of between about 0.1 mm and about 0.6 mm, and a focal spot is between about 0.2 mm and about 0.6 mm.

13. The x-ray CT system of claim 1, wherein the controller is configured to operate the gantry to perform one of a helical scan or spiral scan.

14. The x-ray CT system of claim 1, further comprising an image reconstructor configured to generate an image based on x-rays detected by the x-ray detector using one of derivative backprojection reconstruction, iterative reconstruction or statistical reconstruction.

15. The x-ray CT system of claim 1, wherein the ROI is breasts and wherein the controller is configured to (i) reduce or stop exposure of the ROI to the x-ray beams when a plurality of tissues are between the breasts and the x-ray source and (ii) expose the breasts to the x-ray beams when there is no tissue or a reduced amount of tissue between the breasts and the x-ray source.

16. The x-ray CT system of claim 1, wherein the ROI is a sensitive organ region and the controller is further configured to minimize radiation dose from the x-rays to the sensitive organ region.

17. The x-ray CT system of claim 16, wherein the sensitive organ region comprises a breast region.

18. An x-ray computed tomography (CT) system comprising:
    a rotating gantry;
    a plurality of x-ray sources coupled to the gantry for generating x-ray beams;
    an x-ray detector coupled to the gantry for detecting x-rays of the x-ray beams;
    a controller configured to independently control the plurality of x-ray sources to selectively generate x-ray beams to adjust the focus on a region of interest (ROI) and to control a beam intensity for the x-ray beams generated by the plurality of x-ray sources during a scan; and
    a patient table supporting a patient thereon and wherein the controller is configured to decrease the beam intensity when the plurality of x-ray sources is closer to the ROI of the patient and to increase the beam intensity when the plurality of x-ray sources is farther away from the ROI.

19. The x-ray CT system of claim 18, wherein the controller is configured to adjust one of a tube current or a tube voltage of the plurality of x-ray sources.

20. The x-ray CT system of claim 18, wherein the controller is configured to adjust the focus or beam intensity based on an angular orientation of the rotating gantry.

21. The x-ray CT system of claim 18, wherein the ROI comprises a breast region.

22. The x-ray CT system of claim 18, wherein the ROI comprises a lung region.

23. The x-ray CT system of claim 18, wherein the ROI is a sensitive organ region and the controller is further configured to minimize radiation dose from the x-rays to the sensitive organ region.

24. The x-ray CT system of claim 23, wherein the sensitive organ region comprises a breast region.

25. The x-ray CT system of claim 18, wherein the x-ray detector comprises a photon-counting detector.

26. The x-ray CT system of claim 18, further comprising a patient table and wherein a patient is supported in one of a supine position within a bore of the gantry or a prone position within a bore of the gantry, wherein the patient table includes an opening for receiving breasts of the patient therethrough for the prone position.

27. The x-ray CT system of claim 18, wherein the x-ray detector comprises a plurality of elements having a cell size of between about 0.1 mm and about 0.6 mm, and a focal spot is between about 0.2 mm and about 0.6 mm.

28. The x-ray CT system of claim 18, wherein the controller is configured to operate the gantry to perform one of a helical scan or a spiral scan.

29. The x-ray CT system of claim 18, further comprising an image reconstructor configured to generate an image based on x-rays detected by the x-ray detector using one of derivative backprojection reconstruction, iterative reconstruction or statistical reconstruction.

30. The x-ray CT system of claim 18, wherein the ROI is breasts and wherein the controller is configured to (i) reduce or stop exposure of the ROI to the x-ray beams when a plurality of tissues are between the breasts and the plurality of x-ray sources and (ii) expose the breasts to the x-ray beams when there is no tissue or a reduced amount of tissue between the breasts and the plurality of x-ray sources.

31. A method to control the operation of a rotating computed tomography (CT) imaging system to perform organ specific imaging, the method comprising:
    identifying a patient orientation within a bore of the CT imaging system;
    determining a gantry angle of the CT imaging system, the gantry supporting at least one x-ray source and an x-ray detector;
    adjusting, during a scan with the CT imaging system, a focus of the at least one x-ray source on a region of interest (ROI) and a beam intensity generated by the at least one x-ray source based on an angular orientation of the gantry; and
    decreasing the beam intensity when the at least one x-ray source is closer to the ROI and increasing the beam intensity when the at least one x-ray source is farther away from the ROI.

32. The method of claim 31, wherein adjusting the focus comprises one of adjusting a collimator field of view (FOV) coupled to the at least one x-ray source or selectively adjusting which of a plurality of x-ray sources generates an x-ray beam.

33. The method of claim 31, wherein adjusting the beam intensity comprises adjusting one of a tube current or a tube voltage of the at least one x-ray source.

34. The method of claim 31, further comprising controlling the gantry to perform one of a helical scan or a spiral scan.

* * * * *